United States Patent
Twiss (10) Patent No.: US 9,707,501 B2
(45) Date of Patent: Jul. 18, 2017

(54) DEBRIS FILTER SENSOR

(71) Applicant: Cisco Technology, Inc., San Jose, CA (US)

(72) Inventor: Robert Gregory Twiss, Chapel Hill, NC (US)

(73) Assignee: Cisco Technology, Inc., San Jose, CA (US)

( * ) Notice: Subject to any disclaimer, the term of this patent is extended or adjusted under 35 U.S.C. 154(b) by 0 days.

(21) Appl. No.: 15/423,114

(22) Filed: Feb. 2, 2017

(65) Prior Publication Data
US 2017/0144095 A1 May 25, 2017

Related U.S. Application Data (62) Division of application No. 14/310,176, filed on Jun. 20, 2014, now Pat. No. 9,597,619.

(51) Int. Cl.
| B01D 35/14 | (2006.01) |
| B01D 46/00 | (2006.01) |
| G01N 15/06 | (2006.01) |
| G01N 15/08 | (2006.01) |

(52) U.S. Cl.
CPC ....... B01D 46/0086 (2013.01); B01D 46/008 (2013.01); G01N 15/0618 (2013.01); G01N 15/08 (2013.01); B01D 2279/45 (2013.01); G01N 2015/084 (2013.01)

(58) Field of Classification Search
CPC ...... B01D 35/14; B01D 35/43; B01D 35/435; B01D 46/0086; B01D 46/42; F24F 2011/0093; B60H 2003/0683
See application file for complete search history.

(56) References Cited

U.S. PATENT DOCUMENTS

| 2,524,336 | A | | 10/1950 | Vokes | |
| 4,122,713 | A | * | 10/1978 | Stasz | A61M 1/3626 73/19.1 |
| 5,056,355 | A | | 10/1991 | Hepher et al. | |
| 5,259,245 | A | | 11/1993 | Liu | |
| 5,429,649 | A | * | 7/1995 | Robin | B01D 46/0086 55/309 |
| 5,856,198 | A | * | 1/1999 | Joffe | B01D 53/0454 422/82.01 |
| 6,259,245 | B1 | * | 7/2001 | Toda | G01R 15/20 250/227.18 |
| 2007/0247555 | A1 | * | 10/2007 | Diersing et al. | A01M 1/205 349/6 |
| 2012/0074959 | A1 | * | 3/2012 | Lee et al. | G07D 5/08 324/655 |

OTHER PUBLICATIONS

L.W. Wilson et al, Development of a Personal Dust Monitor with a Piezoelectric Quartz Crystal Sensor, 2004, vol. 8, No. 2, IOP Science Measurement Science and Technology.

\* cited by examiner

*Primary Examiner* — Justin Olamit (57) ABSTRACT

In one embodiment, a piezoelectric device is positioned adjacent to a debris fence. A resonant frequency detection circuit connects with the piezoelectric device. The resonant frequency of the piezoelectric device is responsive to debris adjacent to the debris fence.

17 Claims, 5 Drawing Sheets

DEBRIS FILTER SENSOR

RELATED APPLICATION

The present patent document is a divisional of U.S. patent application Ser. No. 14/310,176, filed Jun. 20, 2014, which is hereby incorporated by reference.

TECHNICAL FIELD

This disclosure relates in general to electronic equipment filtering, and more particularly to sensing debris build-up for replacing filters.

BACKGROUND

Thermal management drives both power and maintenance operational costs. Telecommunications and networking devices primarily rely on thermal management through forced (fan-driven) air cooling. These cooling systems are protected by air filters to help prevent foreign debris (e.g., dust and other particulate matter) from contaminating interior surfaces, causing airflow blockage, and reducing cooling. Over time, air filters become increasingly clogged with debris, occluding system airflow and resulting in increased power usage or decreased thermal efficiency. Air filters are therefore changed manually on a regular basis, which incurs installation costs. Replacing a filter too early or too late both result in unacceptable and/or unneeded additional operation and/or installation costs. This inefficiency is multiplied by hundreds or even thousands of filters in a data center or other large-scale equipment deployments.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts.

DESCRIPTION OF EXAMPLE EMBODIMENTS

Overview

A dust sensor indicates an amount of dust build-up on a filter. For the dust sensor, a piezoelectric device is positioned so that air flowing to the filter passes over the piezoelectric, such as positioned perpendicularly to the filter. Other orientations may be used. Dust build-up on the piezoelectric device causes a shift in resonant frequency of the sensor. By detecting the resonant frequency, the amount of dust build-up is determined. Other detection may be used.

In one aspect, a piezoelectric device is positioned adjacent to a debris fence. A resonant frequency detection circuit connects with the piezoelectric device. The resonant frequency of the piezoelectric device is responsive to debris adjacent to the debris fence.

In another aspect, a filter filters air for a networked computer. The filter is in a first plane. A resonance of a piezoelectric sensor adjacent to the filter is established. The piezoelectric sensor has a largest surface forming a second plane different than the first plane. A frequency of the resonance is measured. An amount of dust on the filter is indicated as a function of the frequency of the resonance of the piezoelectric sensor.

In yet another aspect, a filter of a rack mounted network device is provided. A dust sensor includes a dust screen parallel with the filter and positioned such that air passing to the filter passes through the dust screen and piezoelectric material positioned such that the air passing through the dust screen passes over the piezoelectric material.

EXAMPLE EMBODIMENTS

In data centers, telecommunications complexes, server rooms, information technology locations, or other networking arrangements, multiple filters are provided for thermal management of the different electronics. The filters are to be replaced when sufficient dust build-up occurs. To optimize the thermal efficiency and replacement cost, the timing of replacement of any given filter depends on the amount of dust build-up. For example, filters situated near the floor in one area of a data-center may pick up a disproportionate amount of debris and require more frequent changing than filters mounted higher in a rack elsewhere in the center. It would be advantageous to replace filters only when needed rather than on an estimated schedule.

The need for replacement is based on measurement. The dust and/or debris build-up is measured with a piezoelectric sensor. The sensor is positioned so that air passing to or through the filter passes over the sensor. As a result, dust and/or debris may build up on the sensor as well as the filter. Using a relationship of filter and sensor dust build-up, sensor readings may be used to determine (e.g., estimate) the amount of dust on the filter. For detection, a resonant frequency of the piezoelectric sensor may be measured. As the dust and/or debris builds-up, the resonant frequency changes. Based on calibration, the amount of build-up is mapped to the resonant frequency.

By having the filters indicate when to change, greater optimization may be provided. A low-cost dust and/or debris sensor allows systems operators to optimize air filter maintenance. Rather than replacing in an ad hoc filter-by-filter process, replacement occurs as needed. In a datacenter or other rack mount environment of multiple network devices, any given filter is replaced as needed. The sensor information from each filter may be used to optimize maintenance. A maintenance management system receiving readings from different filters may allow for better maintenance planning.

Figure 1:
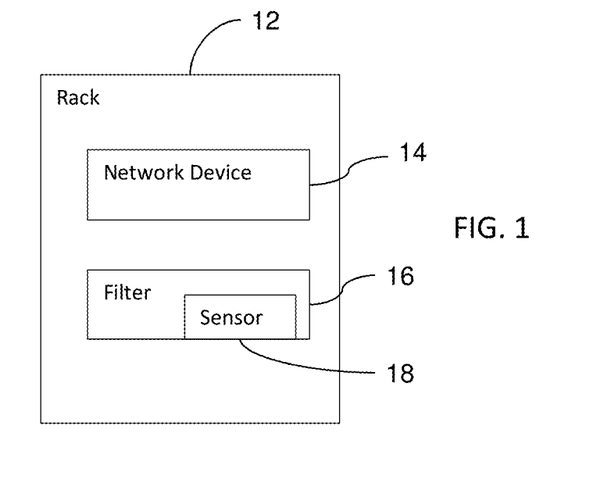
FIG. 1 is a simplified block diagram of an example system for sensing debris build-up on a filter.

FIG. 1 shows a system for sensing debris build-up on a filter. The debris is most likely dust, but may be other particulates. The system is for use in a datacenter, telecommunications complex, server room, or other network or information technologies center. Alternatively, the system is also applicable for standalone applications such as a personal computer or other networking environment.

Additional, different, or fewer components may be provided. Only one rack 12 is shown, but additional racks 12 may be provided. Only one network device 14 is shown, but additional network devices may be provided in the rack 12. Similarly, only one filter 16 is shown, but additional filters may be provided for the rack 12 and/or network device 14. The filter 16 is for a specific network device 14 or for a group of network devices 14.

The rack 12 is a frame for mounting one or more network devices 14. The rack 12 is tin, aluminum, steel, or other metal. Shelves, card slots, or other mounting structures for the network device 14 are included. A back-plane, cable routing, power source, and/or other structure may be provided as part of or connected to the rack 12. Any now known or later developed rack 12 may be used.

The rack 12 supports the network device 14. The network device 14 bolts to, latches to, or rests on the rack 12. In one embodiment, the network device 14 plugs into the rack 12.

The network device 14 is a line card, server, router, switch, or other device used in a computer network. One or more cables connect the network device 14 to other devices on the rack 12, in other racks in a same room, or in remote locations outside the room. Any computer or processor-based device may be used as the network device 14.

The network device 14 generates heat during operation. More optimal operation generally occurs at lower temperatures. To cool the network device 14, air is forced by or through the network device 14. A fan, fan tray, or rack, or other air flow device causes the air to flow to the network device 14. Ducts or other guides may be used to direct the air flow.

The filter 16 is positioned to remove debris, such as dust, from the air being forced through or past the network device 14. Any debris build-up on or in the network device 14 may result in less efficient cooling, causing less optimal operation. By filtering the air, the network device 14 is more likely to continue optimal operation.

The filter 16 is a screen or web of material sized to prevent air-borne debris from passing through. Paper, foam, plastic, metal, fiber glass, or other materials may be used. Any size and corresponding rating of the filter 16 may be provided. For example, a H13 high efficiency particulate air (HEPA) filter is used.

The filter 16 has any size and shape. For example, the filter 16 is flat or has an accordion surface over a planar region. The filter 16 is rectangular, but may be square, circular or other shape.

Screws, latches, or a snap fit hold the filter 16 to the electronic device 14, the rack 12, and/or a sub-assembly housing. In one embodiment, the filter 16 includes a wire screen or metal edges for connection with a housing. The filter 16 is part of the network device 14. In other embodiments, the filter 16 is part of a housing separate from network device 14, such as a filter for an enclosed rack 12 or for a group of network devices 14.

The sensor 18 connects adjacent to the filter 16. The connection is directly to the filter 16, such as being bonded, latched, bolted or screwed to the filter 16 or a framework of the filter 16. Alternatively, the sensor 18 connects to the housing to which the filter 16 is connected, connects to the rack 12, and/or connects to the network device 14. The sensor 18 is connected so that air passing to or through the filter 16 also passes over the sensor.

The sensor 18 is a piezoelectric sensor. Any piezoelectric sensor may be used, such as piezoelectric ceramic, composite, or film. The piezoelectric has multiple electrodes for transducing between vibration or mechanical force and electrical energy. The transduction between mechanical and electrical energies is used to sense debris on the sensor 18. For example, an amplitude of electrical signal generated from a known acoustic or mechanical signal is measured. Smaller amplitude than a calibrated value indicates interference (e.g., debris). As another example, the piezoelectric is part of a feedback or loop arrangement establishing a resonance frequency. The frequency of the resonance may indicate the amount of debris build-up on the sensor 18.

Figure 2:
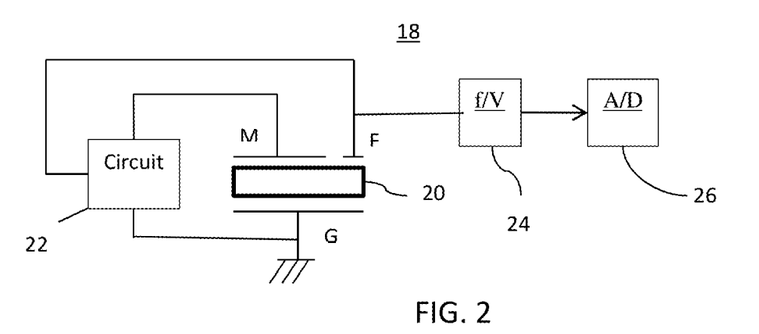
FIG. 2 is a circuit diagram of one embodiment of a system for sensing debris build-up on a filter.

FIG. 2 shows one embodiment of the sensor 18. The sensor 18 includes the piezoelectric device 20 in a resonance circuit 22, a frequency-to-voltage converter 24, and an analog-to-digital converter 26. Additional, different, or fewer components may be provided. For example, a frequency-to-digital converter is provided instead of the separate or discrete converters 24, 26.

The piezoelectric device 20 is any piezoelectric material. In one embodiment, the piezoelectric device 20 is a slab or disk of piezoelectric ceramic of lead zirconate titanate crystals. Other materials with piezoelectric properties may be used. The material may be in any shape, such as a film.

In the example of FIG. 2, the piezoelectric device 20 includes three electrodes M, F, G. The ground electrode G is on an opposite side of the plate-like piezoelectric material from two other electrodes M, F. One electrode F sharing a side with the other electrode M is relatively smaller. For example, the electrode F covers ¼ or less of the surface of that shared side. Any shape of the electrodes may be provided, such as the electrode M surrounding the electrode F or the electrode F being in a slot from one edge to the center of the electrode M. The ground electrode G covers all of one side, but may cover less of the one side. Other arrangements of the electrodes may be used.

With three electrodes, the piezoelectric device 20 is a three-wire feedback piezoelectric sensor. With the three-wire or electrode arrangement, one electrode F operates as a microphone or receiver, and the other electrode M operates as a speaker or transmitter. If both transmit and receive operation occur at a same time, the piezoelectric device provides feed-back to itself. This self-feedback establishes a resonant frequency. The mounting, the circuit 22, and/or any material on the piezoelectric device 20 may result in a different resonance frequency.

In an alternative arrangement, the three-wire or feedback system is created with two two-wire piezoelectric devices. One acts as the transmitter and the other acts as the receiver. For example, a shared ground electrode is between two different slabs or disks of piezoelectric material. The signal electrodes (i.e., one for transmit and the other receive) are on opposite ends of the stack. Other arrangements may be used.

Two-wire or other types of piezoelectric devices may be used without further stacking. For example, vibrations received from a thumper or other acoustic generator are received by a receive electrode. As another example, the piezoelectric device transmits an acoustic signal at one time and then receives echoes from an adjacent structure at a different time. The resulting electrical signal is responsive to the intensity of the received acoustic signals. The amount of dust may result in more or less intensity without use of resonant frequency.

In one example, the resonant circuit 22 includes a transistor with the emitter connected to ground and the collector connected to the transmitter electrode M of the piezoelectric device 20. A direct current voltage connects through one resistor to the source, through another resistor to the receiver electrode F, and through that resistor and another resistor to the gate. While one electrode G is grounded, feedback between the other two electrodes M, F (e.g., speaker to microphone) is created. The arrangement is a Hartley oscillator. Other oscillators may be created. Other circuit arrangements using transistors, resistors, inductors, capacitors, and/ or other components may be provided. Additional, different, or fewer components may be provided.

The resonant circuit 22, in combination with the feedback in the piezoelectric device 20, causes the piezoelectric device 20 to resonate at a given frequency. Any change in mechanical stress, pressure, or connection with the piezoelectric device 20 causes resonance at a different frequency. The oscillation frequency is dependent on the mechanical vibrational properties of the piezoelectric device 20. If material such as dust or other debris accumulates on the piezoelectric device 20, the oscillator automatically operates at a different frequency, such as a lower frequency for more dust. Additional accumulation further changes this resonant frequency. These lowering frequencies may be compared to a clean initial (e.g., setup or calibration) frequency to determine increased debris accumulation.

The converters 24, 26 detect the resonant frequency. The circuit 22, piezoelectric device 20, and converters 24, 26 form a system for detection of dust or debris accumulation. The resonant frequency detection circuit is part of the sensor 20 and detects the resonant frequency.

In the embodiment of FIG. 2, the frequency-to-voltage converter connects with one of the electrodes F of the piezoelectric device 20. Other connections may be used, such as with a different electrode M or other part of the circuit 22.

The frequency-to-voltage converter 24 is an integrated circuit or discrete component. In one embodiment, the frequency-to-voltage converter 24 is a series of amplifiers, one shot, and transistor. The frequency-to-voltage converter 24 is an analog device, but may alternatively have a digital output. Any now known or later developed circuit for outputting a signal (e.g., voltage or current) indicating the frequency of an input signal may be used. Linear or non-linear relationship between frequency and output may be provided. The frequency-to-voltage converter 24 measures the resonant frequency. The frequency is converted to a value (e.g., voltage) representing the frequency.

The analog-to-digital converter 26 is any now known or later developed analog-to-digital converter. Any number of bits may be output, such as a 4 or 8 bit output. In alternative embodiments, the analog-to-digital converter 26 is not a discrete component but is instead integrated with the frequency-to-voltage converter 24.

The analog-to-digital converter 26 converts the voltage or other output of the frequency-to-voltage converter 24 to digital form for communicating with a computer, for sending a message, and/or for generating an alarm. The voltage or other signal representing the resonance frequency is converted into digital form for further processing and/or communications.

The circuit 22 (other than the piezoelectric device 20) and/or converters 24, 26 are positioned adjacent to or in a housing with the piezoelectric device 20. Alternatively, the circuit 22 (other than the piezoelectric device 20) and/or the converters 24, 26 are positioned in the network device 14, the rack 12, and/or elsewhere. Wires connect the piezoelectric device 20 to the reminder of the circuit and/or converters 24, 26.

The piezoelectric device 20 is positioned to intercept dust or otherwise collect debris to which the filter 16 is exposed. In one embodiment, a largest surface or side of the piezoelectric device 20 is positioned on and parallel with the filter 16. As air passes to or through the filter 16, some of the air passes beside and/or over the piezoelectric device 20, resulting in accumulation of some or even less debris on the piezoelectric device 20 than the filter 16.

In another embodiment, the piezoelectric device 20 is oriented in a non-parallel arrangement with the filter 16. For example, the piezoelectric device 20 is a disk or slab with a largest surface or side. This largest surface is oriented to be parallel with the air flow or perpendicular to the filter 16. Air passing to or through the filter 16 travels across or over this largest surface. Due to eddies, static electricity, or other process, some of the debris is deposited on the piezoelectric device 20. Other non-parallel and non-perpendicular arrangements of the planes in which the largest sides of the filter 16 and piezoelectric device 20 exist may be used.

Figure 3:
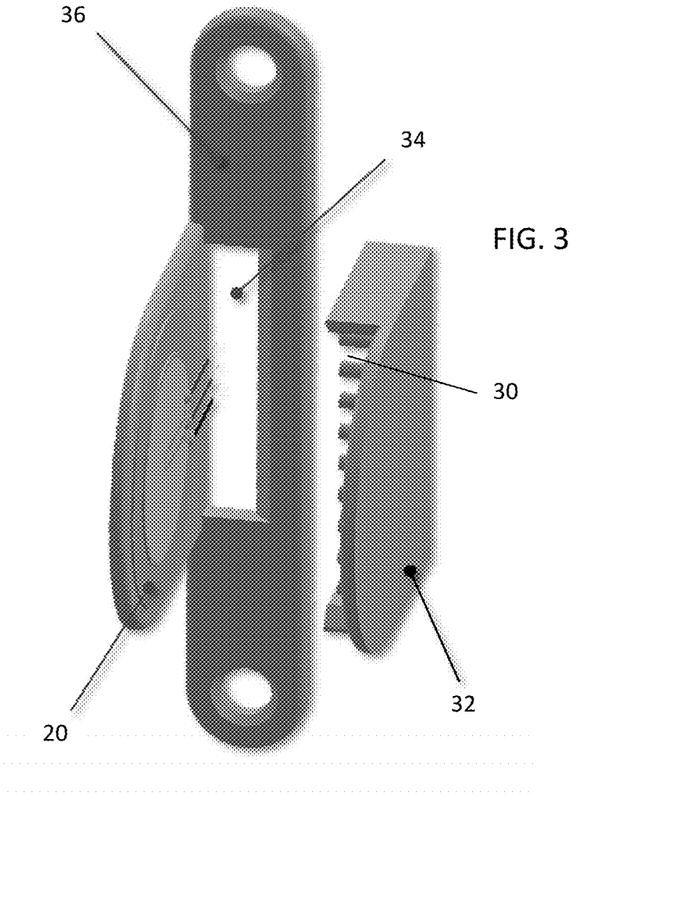
FIG. 3 is an exploded view of one embodiment of a system for sensing debris build-up on a filter.
Figure 4:
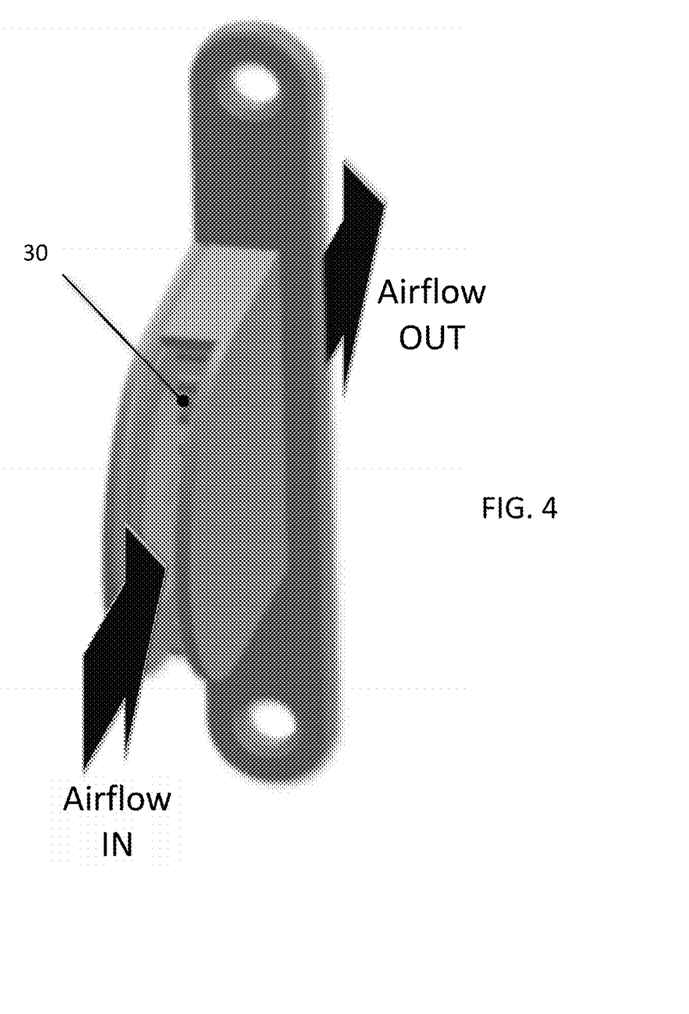
FIG. 4 is a perspective view of the embodiment of FIG. 3 as assembled.

FIGS. 3 and 4 show a further embodiment of the piezoelectric sensor 18. To assist in accumulation of debris adjacent the piezoelectric device 20 more similar to accumulation on the filter 16, a dust screen 30 is provided. FIGS. 3 and 4 show one approach with a cover 32, air slot 34 and base 36. Other approaches with or without the cover 32 and/or base 36 may be provided.

The dust screen 30 is a fence or other structure for partially blocking and partially allowing flow of air. In one embodiment shown in FIGS. 3 and 4, the dust screen 30 is formed from parallel slats, but crossing, mesh, circular perforations, hexagonal perforations, or other arrangements may be used.

The piezoelectric device 20 is positioned adjacent to the dust screen 30. For example, the slats of the dust screen 30 are positioned to be perpendicular to but spaced from the largest or exposed surface of the piezoelectric device 20. The spacing avoids mechanical contact of the slats with the piezoelectric device 20. Other angles and/or with contact may be provided. The air passing over the piezoelectric device 20 may deposit debris on the exposed or largest surface with or without the dust screen 30.

The dust screen 30 is positioned to be parallel with the plane of the largest side or extent of the filter 16. Non-parallel arrangement may be used. Air passing through the dust screen 30 also then passes through the filter 16. Alternatively, the filter 16 includes an aperture filled by the dust screen 30.

The piezoelectric device 20 is positioned to be parallel with the flow of air or perpendicular to the dust screen 30. The slats cause turbulence but pass some debris. The turbulence results in deposit of dust or debris on the piezoelectric device 20. Alternatively, the dust screen 30 has smaller holes or pass through regions, such as the same or smaller size than the filter 16. As dust or debris accumulate against the dust screen 30, some debris or dust contacts the piezoelectric device 20, such as falling from the accumulation against the dust screen 30 onto the surface of the piezoelectric device 20.

The base 36 is a mounting plate for mounting the sensor 18 to the filter 16 or adjacent to the filter 16. Screw or bolt holes are shown for mounting the sensor 18 to the filter 16 or a housing. Latches, adhesive bonding, or other attachment may be used. The connection positions the air slot 34 against or spaced from the filter 16. Some of the air flow through the filter 16 passes through the sensor 18.

The base 36 includes an air slot 34, holds the cover 32, and holds the piezoelectric device 20. The base 36 may or may not include other parts of the sensor 18. The base 36 connects with the dust screen 30 (e.g., through the cover 32) and the piezoelectric device 20.

The air slot 34 is for passing air through the dust screen 30 to the filter 16. The air slot 34 is of any size, such as having a length similar or the same as the diameter or length of the piezoelectric device 20 (e.g., air slot of 1 inch by ½ inch). The height of the air slot 34 is less than the length, but may be the same or greater.

The cover 32, in combination with the piezoelectric device 20, forms a partial duct or guide for the air over the piezoelectric device 20 and through the dust screen 30. More or less guidance or ducting may be provided.

The cover 32 and base 36 are shown as separate devices. The cover 32 may be bonded to or sonic welded with the base 36. Other connections may be used, such as screws or bolts. In another embodiment, the cover 32 and base 36 are formed as one part. The dust screen 30 is formed as part of the cover 32, but may be part of the base 36 or a separate part. Additionally, the cover 32 and base 36 may include holes or other apertures that may be used to introduce a compressed gas stream or vacuum to allow cleaning of dust screen 30.

Any material may be used for the cover 32 and base 36, such as plastic. In one embodiment, a glass-filled ABS plastic is used. In one embodiment, the base 36 or the part of the base 36 supporting the piezoelectric device 20 is brass, tin, or other metal.

The piezoelectric device 20 connects to or is housed by the base 36. A spring, silicone, gasket, O-ring, or other elastic connection may be used. In one embodiment, the piezoelectric device 20 is flexibly connected to limit alteration of the resonant frequency due to the base 36. In alternative embodiments, a fixed or rigid connection is used.

The sensor 18 is sized to be smaller than the filter 16, such as covering 1/10 or less of the filter area. For example, the filter has a 1 foot×4 inch filter area (e.g., hole in the housing) through which air flows. The air slot 34 of the sensor 18 is about 1 inch by ⅓ inch. Other relative sizes may be used, including the air slot 34 being a same size as the filter area.

The sensor 18 is positioned in front of the filter 16. The sensor 18 is mounted to the filter 16. Alternatively, the sensor 18 is mounted to a housing, to the rack 12, or to a mount bracket adjacent the filter 16 and extends over the filter 16. No or little spacing (e.g., less than ¼ an inch) is provided between the air slot 34 and the filter 16, but larger spacing may be used, such as where the air is guided through a duct to the filter 16.

FIG. 4 shows the assembled sensor 18. Air flows through the dust screen 30 and over the piezoelectric device 20. Airflow enters the front slot and exits the rear air slot 34 of the base 36. The dust screen 30 mimics a filter material that allows air to move through relatively freely but will help capture particulate matter. Captured material eventually impacts the piezoelectric device 20 and alters the system resonant frequency.

In one embodiment, the sensor 20 is added to an existing filter 16, rack 12, and/or network device 14. As part of a retrofit of an existing facility, the sensors 20 are added. The sensor 20 is added to a filter 16 already in place. Alternatively, the sensor 20 is integrated with or manufactured as part of the filter 16, rack 12, and/or network device 14. For example, a filter 16 is to be initially placed or is to replace a previous filter. The new filter 16 includes the sensor 20.

Figure 5:
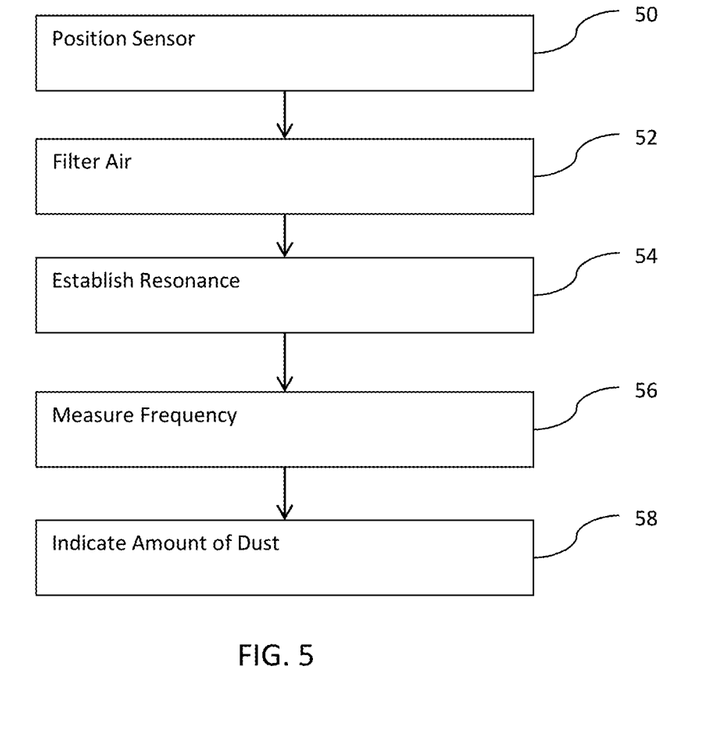
FIG. 5 is a flow chart diagram of one embodiment of a method for sensing debris build-up on a filter.

FIG. 5 shows a method for sensing accumulation of debris on a filter. The acts are performed using a piezoelectric sensor on a filter in a datacenter or other computer networking environment. For example, the acts are performed for each of a plurality of sensors on corresponding racks or stacks of network computers.

Various acts 50-58 are shown in FIG. 5. Additional, different, or fewer acts may be performed. For example, act 50 is not performed as the sensor is already positioned by a filter. As another example, acts 54 and 56 are replaced with magnitude of acoustic signal measurement or other measurement transducing mechanical energy into electrical energy. In yet another example, acts for communicating and/or using the dust accumulation information are performed.

The acts are performed in the order shown, as represented vertically with the first acts occurring at the top of FIG. 5. In other embodiments, other orders are provided, such as performing the filtering of the air in act 52 at any time or constantly while performing any of the other acts.

In act 50, the debris or dust sensor is positioned. Dust is debris. The sensor is positioned to detect debris for a filter. The debris on the filter itself may not be detected, but the amount of debris that is likely to be on the filter is detected.

To detect the amount of debris, the sensor is positioned to be exposed to the same or similar air as the filter. The sensor is positioned adjacent to, within a same duct, and/or within a same air flow as the filter. Air that is to pass through the filter also passes by or through the sensor prior to passing through the filter. Only some or all of the air that is to be filtered passes over or through the sensor.

The sensor is positioned in a same plane as the filter. The filter is plate-like or has an orientation. The orientation of the filter establishes a plane. The largest or larger surface or physical extent of the filter defines a plane. In other embodiments, the filter is formed over or as a curved surface or a surface with one or more angles. As such, the filter still defines a plane perpendicular or orthogonal to an average angle of incidence of the air to the filter.

The plane of the sensor is perpendicular (e.g., 90 degrees) or other non-0 angle to the plane of the filter. In an alternative embodiment, sensor is positioned to have a largest or larger surface parallel with the plane of the filter. For example, the sensor rests on or against the filter with a longer length and width being in the parallel plane and a shorter height being orthogonal to the plane.

The orientation of the sensor is based on the orientation of a piezoelectric material of the sensor. Where a plate like piezoelectric sensor (e.g., disk or slab) is used, the largest surface defines the plane of the sensor. Alternatively, the exposed part of the piezoelectric sensor defines the plane of the sensor. Where a film or composite is used, the largest surface may be curved or include angles. As such, the average orthogonal angle over the largest or exposed surface defines an orthogonal angle to the plane of the sensor.

By positioning the piezoelectric sensor to be perpendicular to the filter, the air flow passes or flows over the largest or exposed surface of the piezoelectric sensor. Rather than blocking the air or causing a change in direction of the air more than 20 degrees on average, the sensor allows the air to pass in parallel to the plane of the sensor. In alternative embodiments, the piezoelectric portion of the sensor impedes the air flow.

The positioning is performed by manufacture of the filter and/or by installation by a maintenance person. For example, the sensor is positioned by a person attaching the sensor to the filter, a housing, or both. As another example, the sensor is part of or made with the filter. By installing the filter, the sensor is positioned with the filter.

In act 52, air is filtered. In a data center or other computer network environment, one or more fans force movement of the air. The air flows through one or more filters, including at least one filter with an adjacent sensor. As a result, any networked computers in the information technology environment are cooled. The air flowing by, through, or over the networked computer absorbs convected heat from the networked computer and carries the heat away. The filter removes some or all debris from the air to prevent debris build-up on electronics.

In act 54, a resonance of the piezoelectric sensor is established. The piezoelectric is used to both create vibration and the measure the vibration. This creates a feedback loop. By connecting a circuit, the piezoelectric sensor is caused to resonate. For example, the piezoelectric sensor is included as a component in a Hartley oscillator. By applying power to the piezoelectric sensor, vibrations are created. The vibrations are also received or detected by the piezoelectric sensor.

The oscillation frequency is the resonant frequency. The frequency of the resonation depends on the amount of vibration and any damping of the vibration between the transmission and reception. Differences in load on the piezoelectric sensor result in differences of the resonant frequency.

In act 56, the frequency is measured. The resonant frequency of the oscillator formed with the piezoelectric sensor is measured. Any measurement of the frequency may be used. For example, a circuit counts a number of peaks or zero crossing relative to an oscillator with a known frequency. Other frequency measures may be used.

Resonant frequency measurements may occur at pre-set or calculated intervals. For example, measurements are performed at equal time intervals. The frequency of measurements may increase or decrease based on comparing the resonant frequency measurement to established "clean sensor" baseline or other calibration measurements. For example, as the resonant frequency indicates further debris, the frequency of the measurements is increased.

The output of the resonant circuit may be filtered. For example, signals having amplitudes at frequencies other than the frequency with the greatest amplitude are reduced or eliminated.

The frequency measurement results in a digital or analog indication of the resonant frequency. Analog measures may be converted to digital samples. The resonant frequency is converted to digital data. The digital or analog information may be used for further processing and/or storage and retrieval.

In act 58, the amount of dust on the filter is indicated. The dust from the air passing by the sensor accumulates on the sensor. The accumulation may be the same, more or less than the accumulation on the filter. Since the same air is passing both the sensor and the filter, measuring the accumulation of debris on the sensor represents the accumulation on the filter. For example, air with a greater amount of dust results in greater accumulation on the filter as well as the sensor. Air with a lesser amount of dust results in relatively lesser accumulation on the filter as well as the sensor.

The output of the measurement of act 56 indicates the amount of dust or other debris on the filter. For example, the frequency of resonance of the piezoelectric sensor indicates the amount. As initially installed and/or calibrated, the sensor has a given resonance. Dust or other debris causes the resonance frequency to shift, such as shifting downward. The amount of shift or the value of the resonance frequency indicates an amount of dust or debris.

In one embodiment, the measured frequency is compared to a threshold. The threshold is based on an initial or calibrated frequency for the sensor. The sensor itself is installed or as manufactured before installation is used for calibration. Alternatively, an average or calibration for the type of sensor is used.

The threshold for any given amount of dust is set based on empirical data. For example, the threshold is set as a percentage of the initial or calibrated value. As another example, the threshold is set as a difference from the initial or calibrated value. When the measured frequency is at or below the threshold, then an amount of dust corresponding to that threshold is indicated. The threshold may be set at a level of accumulation for which replacement or cleaning of the filter is recommended. A change of the filter is indicated where the frequency is lower than the threshold. In alternative embodiments, the frequency increases with greater accumulation.

The indication is an output of the comparison to the threshold or a sequence of thresholds. The output is provided as a value, alarm, and/or message. For example, a message indicating that the filter is becoming clogged and/or a message to replace the filter is generated. Rather than a computer message, the indication may be a light or sound. Alternatively, the measure of frequency itself is the output.

A processor, operable to execute instructions or logic stored in a non-transitory computer readable storage medium, is configured to apply the threshold. Alternatively, a circuit, application specific integrated circuit, or other arrangement applies the threshold. The measured frequency and/or amplitude information from the sensor is used to communicate accumulation level to a user, processor, or display.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method comprising:
   filtering, with a filter, air for a networked computer, the filter being in a first plane;
   establishing a resonance of a piezoelectric sensor adjacent to the filter, the piezoelectric sensor having a largest surface forming a second plane different than the first plane, all of the largest surface being non-parallel with the first plane;
   measuring a frequency of the resonance; and
   indicating an amount of dust on the filter as a function of the frequency of the resonance of the piezoelectric sensor.

2. The method of claim 1 wherein establishing comprises establishing the resonance with a Hartley oscillator including three electrically isolated connections with the piezoelectric sensor.

3. The method of claim 1 wherein establishing comprises generating vibrations with the piezoelectric sensor and detecting the vibrations with the piezoelectric sensor.

4. The method of claim 1 wherein measuring the frequency comprises converting the frequency to digital data.

5. The method of claim 1 wherein indicating comprises comparing the frequency to a calibrated threshold, and indicating the amount of dust as corresponding to a change of the filter where the frequency is lower than the calibrated threshold.

6. The method of claim 1 further comprising positioning the second plane perpendicular to the filter so that the air flows over the largest surface in passing through or to the filter.

7. The method of claim 1 further comprising connecting a debris fence distributed along a third plane parallel with the first plane, wherein the second plane is perpendicular to the first and third planes.

8. The method of claim 7 further comprising connecting the debris fence and piezoelectric sensor with a mounting plate such that the third plane is parallel with the first plane.

9. The method of claim 8 further comprising connecting the mounting plate against the filter.

10. The method of claim 7 wherein the debris fence has a largest side formed from structure and gaps of the debris fence, the largest side of the debris fence defining the third plane.

11. A system comprising:
   a filter of a rack mounted network device; and
   a dust sensor comprising:
      a dust screen parallel with the filter and positioned such that air passing to the filter passes through the dust screen; and
      piezoelectric material positioned such that the air passing through the dust screen passes over the piezoelectric material, wherein the piezoelectric material has a largest surface all of which is non-parallel to a largest surface of the filter.

12. The system of claim 11 wherein the largest surface forming a plane perpendicular to the dust screen.

13. The system of claim 11 wherein the piezoelectric material comprises a piezoelectric disk.

14. The system of claim 11 wherein the dust screen comprises a dust fence, the dust fence and piezoelectric material connected to a base connectable with the filter, filter cover, or housing adjacent the filter.

15. The system of claim 11 wherein the piezoelectric material comprise a three-wire feedback piezoelectric sensor;
   further comprising a resonance detection circuit connected with the three-wire feedback piezoelectric sensor.

16. The system of claim 14 wherein the base connects against the filter.

17. The system of claim 11 wherein the dust screen has a largest side formed from structure and gaps of the dust screen, the largest side of the dust screen defining a first plane parallel with the filter.

* * * * *